United States Patent
Mann

(10) Patent No.: US 6,550,326 B2
(45) Date of Patent: Apr. 22, 2003

(54) PORTABLE CONTAINER LEVEL INDICATOR

(76) Inventor: Ken Mann, Box 158, Dinsmore, Saskatchewan (CA), S0L 0T0

( * ) Notice: Subject to any disclaimer, the term of this patent is extended or adjusted under 35 U.S.C. 154(b) by 0 days.

(21) Appl. No.: 09/754,476

(22) Filed: Jan. 4, 2001

(65) Prior Publication Data

US 2001/0008084 A1 Jul. 19, 2001

(30) Foreign Application Priority Data

Jan. 14, 2000 (CA) ............................................. 2296125

(51) Int. Cl.[7] ............................. G01F 23/00; A61B 5/12
(52) U.S. Cl. ....................... 73/290 V; 93/290 R; 93/585
(58) Field of Search ................................ 73/1.73, 1.82, 73/290 V, 585

(56) References Cited

U.S. PATENT DOCUMENTS

| 4,403,508 A | 9/1983 | Langlois |
| 4,480,468 A | * 11/1984 | Sinha ......................... 73/290 V |
| 4,583,405 A | * 4/1986 | Simmons ...................... 73/584 |
| 4,790,183 A | 12/1988 | Pfost |
| 5,409,300 A | * 4/1995 | Bourgoin ...................... 299/69 |

* cited by examiner

Primary Examiner—Daniel S. Larkin
Assistant Examiner—Rodney Frank
(74) Attorney, Agent, or Firm—Patterson, Thuente, Skaar & Christensen, P.A.

(57) ABSTRACT

A portable container level indicator comprises a frame having an upper end and a lower end, and adapted to move along a generally vertical wall surface; an elongate handle having a frame end and a grip end, the frame end pivotally attached to the frame such that the angle between the frame and the handle may vary; a tapping mechanism attached to the frame and operable to propel a tapping member towards the wall surface such that the tapping member contacts the wall surface and generates a sound; and a. trigger located adjacent to the grip end of the handle for operating the tapping mechanism. The sound is audible to the operator and may be amplified if necessary.

6 Claims, 2 Drawing Sheets

PORTABLE CONTAINER LEVEL INDICATOR

This invention is in the field of indicators for determining the level of contents in a bulk storage container and in particular such an indicator that is portable and allows the operator to determine the level of contents while standing at ground level outside of the container.

BACKGROUND

It is often required to find the vertical level of contents in a container. The contents may-be granular or particulate material such as grain or fertilizer in a bin, or a liquid such as fuel in a tank.

There are presently numerous indicators for indicating the level of contents in a container. They range from a simple liquid sight glass on a tank to complex and highly accurate acoustic systems such as are found in U.S. Pat. No. 4,790,183 to Pfost et al. and in U.S. Pat. No. 4,403,508 to Langlois.

The problem with these prior art indicators is that there generally must be a sensor of some sort mounted in each container. Time, expense and planning is required in order to achieve the result. An easily portable and inexpensive indicator that would indicate the level of contents, liquid or granular, in the majority of containers with reasonable accuracy would be beneficial in many situations. All that is often required is an estimate of the contents. For example a farmer could easily find out if a bin was half full or three quarters full and thereby estimate the contents. Where the same indicator could work as well to determine the level in a liquid fertilizer or fuel tank, convenience and economy would be enhanced.

SUMMARY OF THE INVENTION

The invention is based on the well known phenomena that the level of contents in a single wall container may be determined by tapping on the wall. Above the contents boundary there is a hollow sound, while below the boundary there is different solid sound. The phenomena is present where the contents are granular or liquid, and where the wall material is metal, wood or any similar sheet material. The difference in sounds is discernable to the human ear with little difficulty.

It is the object of the present invention to provide a portable container level indicator that is simple and economical, and that provides an indication of the level of the contents of a container from the ground level outside the container.

It is a further object of the present invention to provide such an indicator which generates a sound by tapping on the wall of the container. The sound will generally be audible to the operator standing on the ground, but may include electronic pick-up means to transmit the sound to the operator. The tapping mechanism may be electrical, such as a solenoid propelled tapper, or mechanical, such as a spring propelled tapper.

DESCRIPTION OF THE DRAWINGS

While the invention is claimed in the concluding portions hereof, preferred embodiments are provided in the accompanying detailed description which may be best understood in conjunction with the accompanying diagrams where like parts in each of the several diagrams are labeled with like numbers, and where:

DETAILED DESCRIPTION OF THE ILLUSTRATED EMBODIMENTS

Figure 1:
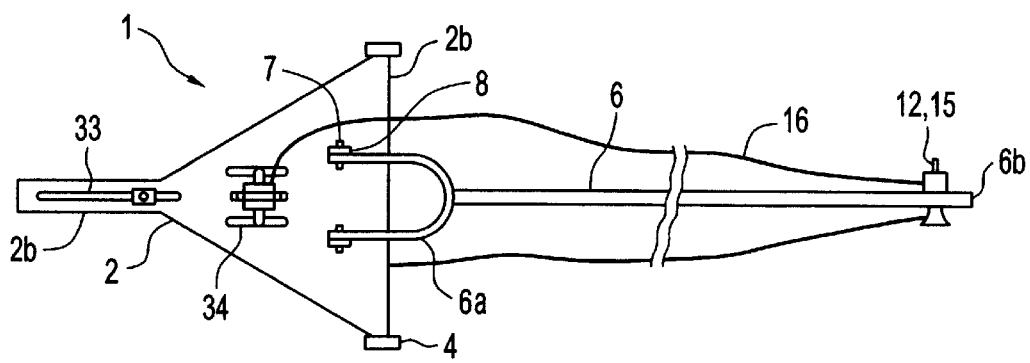
FIG. 1 is a side view of an embodiment comprising wheels and an electric solenoid tapping mechanism.
Figure 2:
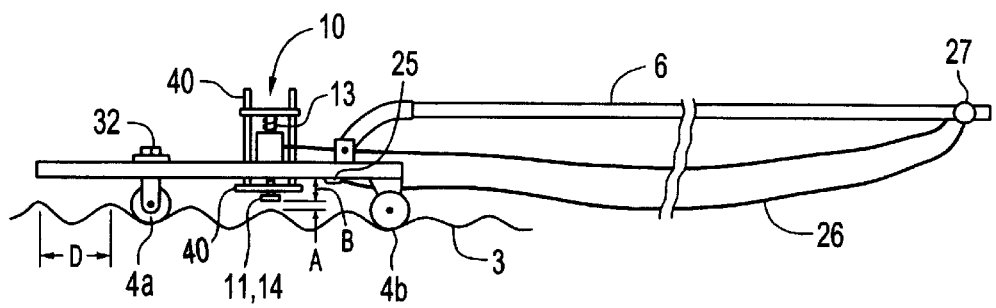
FIG. 2 is an end view of the embodiment of FIG. 1 on a corrugated wall surface.

FIGS. 1–6 illustrate a portable container level indicator 1. A frame 2 has an upper end 2a and a lower end 2b, and is adapted to move along a generally vertical wall surface 3 by attached wheels 4, as illustrated in FIGS. 1 and 2, or skid members such as the skid bumps 5 illustrated in FIGS. 3 and 4. FIG. 7 illustrates a frame 2 with turned up ends so that same forms a skid plate. Many other configurations would as well adapt the frame 2 for movement along a wall surface 3.

Figure 6:
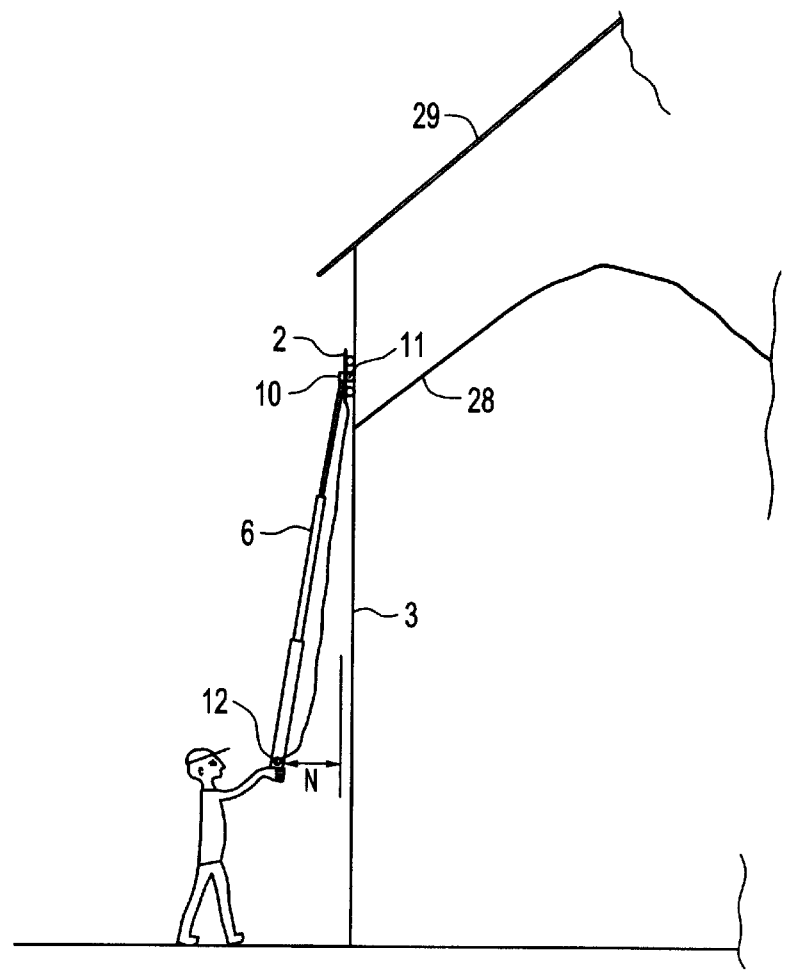
FIG. 6 is a schematic showing the indicator in use on a grain bin.
Figure 7:
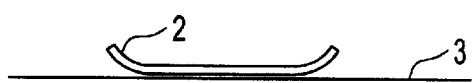
FIG. 7 is an end view of a frame in the form of a skid plate.

An elongate handle 6 has a frame end 6a pivotally attached to the frame 2 by handle pins 7 on brackets 3 such that the angle N between frame 2 and handle 6 may vary as the operator moves the indicator 1 up and down the vertical wall surface 3 as illustrated in FIG. 6.

A tapping mechanism 10 i s attached to the frame 2 and operates to propel a tapping member 11 towards the wall surface 3 such that same contacts the wall surface 3 and generates a sound. A trigger 12 located adjacent to the grip end 6b of the handle 6 operates the tapping mechanism 10.

In the embodiment illustrated in FIGS. 1 and 2 the tapping mechanism 10 comprises an electric solenoid 13 to propel the tapping member 11 being in this case screw head 14. The electric solenoid 13 is controlled and operated by switch 15 15 connected thereto by wire 16. The switch 15 acts as the trigger 12. When the switch 15 is pressed, the solenoid 13 propels th e s crew head. 14 against the wall surface 3, generating a sound.

Figure 3:
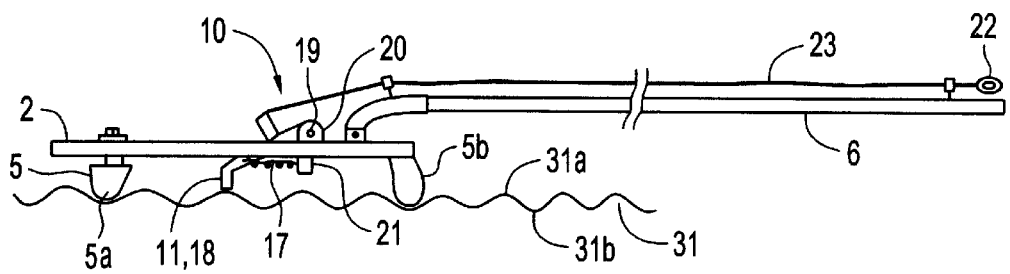
FIG. 3 is an end view of an embodiment comprising skid bumps and a spring tapping mechanism on a corrugated wall surface.
Figure 4:
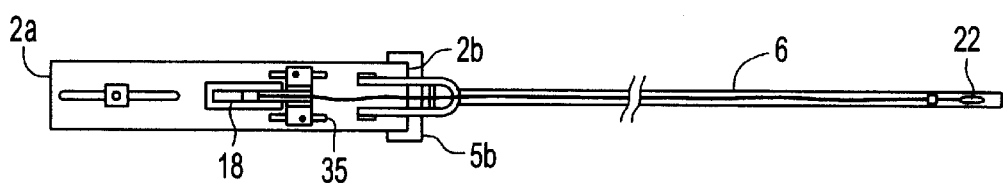
FIG. 4 is a side view of the embodiment of FIG. 3.

In the embodiment illustrated in FIGS. 3 and 4 the tapping mechanism 10 comprises a spring 17 to propel the tapping member 11, being in this case a hammer 18 pivotally attached at one end by hammer pin 19 to a pair of hammer brackets 20 fixed to frame 2. The spring 17 is anchored to a mid-point of the hammer 18 at one end and to a spring bracket 21 fixed to the frame 2 at the opposite end. The hammer 18 is controlled and operated by pulling on the ring 22 on the end of cable 23, the other end of which is attached to the hammer 18. The ring 22 acts as the trigger 12. The operator pulls the ring 22 which lifts the hammer 18 and applies a biasing force to the spring 17. When the ring 22 is released, the spring 17 propels the hammer 18 against the wall surface 3, generating a sound.

Generally the sound will be audible to an operator holding said grip end 6a of the handle 6. Where the handle 6 is very long, or where there is considerable ambient noise, an electronic audio pick-up 25 may be mounted on the frame 2 adjacent to the tapping mechanism 10 in order to pick-up the sound and transmit it through wire 26 to speaker 27 where it can be heard by the operator.

The sound of the tapping member 11 striking the wall surface 3 above the content level 28 in the bin 29 is a hollow sound, while the sound of it striking below the content level 28 is a solid sound. This difference in sound is well known and discernable to the operator.

In FIGS. 1–2 the frame 2 comprises wheels 4 attached thereto for supporting same for movement along the wall surface 3. The illustrated wall surface 3 is horizontally corrugated and so to be effective the indicator 1 is adjustable so that the distance between an upper wheel 4a and a lower wheel 4b same may be made equal to a multiple of the distance D between the horizontal corrugations 31 of the wall surface 3. Thus when the upper wheel 4a is in the bottom 31b of a horizontal corrugation 31, the lower wheel 4a is also in the bottom of a horizontal corrugation 31. This adjustment is made by loosening clamp nut 32 and sliding the upper wheel 4a along frame slot 33.

In order to accommodate different distances D for different bins, the location of the tapping mechanism 10 relative to the wheels 4 is adjustable so that when the upper wheel 4a is in the bottom 31b of a horizontal corrugation and the lower wheel 4b is in the bottom 31b of a horizontal corrugation, the tapping member 11 can be positioned to strike the top 31a of an intermediate horizontal corrugation. This adjustment is made by loosening the bolts holding the electric solenoid 13 to the frame 2 and sliding same along solenoid slots 34.

Similarly in the embodiment of FIGS. 3 and 4, the skid bumps 5 are shaped to follow the horizontal corrugations as they skid along the wall surface 3 so that the operator can feel when the indicator 1 is properly located, the same as with the wheeled embodiment. The distance between the upper and lower skid bumps 5a, 5b is adjusted by sliding the upper skid bump 5a along frame slot 33. The adjustment of the location of the tapping mechanism 10 is made by loosening the bolts holding the hammer brackets 20 to the frame 2 and sliding same along hammer slots 35.

Figure 5:
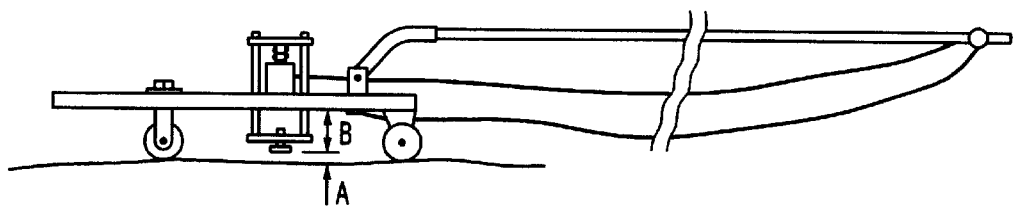
FIG. 5 is an end view of the embodiment of FIG. 1 on a flat wall surface.

To allow the embodiment of FIGS. 1 and 2 to be used on a flat wall surface 3, such as that illustrated in FIG. 5, or one with corrugations of a different depth, the distance B between the at rest position of the tapping member 11, being the screw head 14, as illustrated in FIG. 2 and the frame 2 may be adjusted so that the distance A between the at rest position of the screw head 14 and the wall surface 3 may be kept reasonably constant, so that the screw head is propelled substantially the same distance A before contacting the wall surface 3. This can be accomplished by turning the screw head 14 in or out of the lower plate 40, or by adjusting the length of the lower plate bolts 41 to move the lower plate 40 with respect to the frame 2.

The illustrated adjustment means for orienting the wheels 4, skid bumps 5, and tapping member 11 properly with respect to the corrugations are indicative only of the type of adjustments that would be advantageous in certain applications, and many other means could readily be substituted therefor.

As illustrated in FIG. 6, the handle 6 may be telescopic so that the length of thereof may be adjusted.

The foregoing is considered as illustrative only of the principles of the invention. Further, since numerous changes and modifications will readily occur to those skilled in the art, it is not desired to limit the invention to the exact construction and operation shown and described, and accordingly, all such suitable changes or modifications in structure or operation which may be resorted to are intended to fall within the scope of the claimed invention.

I claim:

1. A portable container level indicator comprising:
   a frame having an upper end and a lower end, and adapted to move along a generally vertical wall surface of a container;
   an elongate handle having a frame end and a grip end, said frame end pivotally attached to said frame such that an angle between said frame and said handle can vary;
   a tapping mechanism attached to said frame and operable to propel a tapping member towards said wall surface such that said tapping member contacts said wall surface and generates a sound that is audibly different above and below a level of particulate material inside the container;
   a trigger located adjacent to said grip end of the handle for operating said tapping mechanism such that as the frame is moved upwards along the container wall surface with the handle, the operator can tap the container wall surface to determine at what point on the container wall the sound changes, thereby determining a level of material in the container;
   wherein said frame comprises wheels attached thereto for supporting same for movement along said wall surface.

2. The indicator of claim 1 wherein said wall surface is horizontally corrugated, and wherein a distance between an upper wheel and a lower wheel is adjustable such that same may be made equal to a multiple of a distance between horizontal corrugations of the wall surface.

3. The indicator of claim 2 wherein a location of said tapping mechanism relative to said wheels is adjustable such that when said upper wheel is in a bottom of a first horizontal corrugation and said lower wheel is in a bottom of a second horizontal corrugation, said tapping member strikes a top of an intermediate horizontal corrugation.

4. A portable container level indicator comprising:
   a frame having an upper end and a lower end, and adapted to move along a generally vertical wall surface of a container;
   an elongate handle having a frame end and a grip end, said frame end pivotally attached to said frame such that an angle between said frame and said handle can vary;
   a tapping mechanism attached to said frame and operable to propel a tapping member towards said wall surface such that said tapping member contacts said wall surface and generates a sound that is audibly different above and below a level of particulate material inside the container;
   a trigger located adjacent to said grip end of the handle for operating said tapping mechanism such that as the frame is moved upwards along the container wall surface with the handle, the operator can tap the container wall surface to determine at what point on the container wall the sound changes, thereby determining a level of material in the container;
   wherein said frame comprises skid members attached thereto for supporting same for movement along said wall surface.

5. The indicator of claim 4, wherein said wall surface is horizontally corrugated, and wherein said skid members are bumps that are shaped to follow said horizontal corrugations and wherein a distance between an upper bump and a lower bump is adjustable such that same may be made equal to a multiple of a distance between horizontal corrugations of the wall surface.

6. The indicator of claim 5 wherein a location of said tapping mechanism relative to said bumps is adjustable such that when said upper bump is in a bottom of a first horizontal corrugation and said lower bump is in a bottom of a second horizontal corrugation, said tapping member strikes a top of an intermediate horizontal corrugation.

* * * * *